United States Patent [19]
Hudson et al.

[11] Patent Number: 6,140,093
[45] Date of Patent: *Oct. 31, 2000

[54] POLYNUCLEOTIDES ENCODING PARAOXONASE

[75] Inventors: Peter L. Hudson, Germantown; Wei Wu He, Columbia; Steven M. Ruben, Olney, all of Md.

[73] Assignee: Human Genome Sciences, Inc., Rockville, Md.

[*] Notice: This patent is subject to a terminal disclaimer.

[21] Appl. No.: 09/067,089

[22] Filed: Apr. 27, 1998

Related U.S. Application Data

[62] Division of application No. 08/783,889, Jan. 16, 1997, Pat. No. 5,792,639, which is a division of application No. 08/270,583, Jul. 5, 1994, Pat. No. 5,629,193.

[51] Int. Cl.[7] ..................................................... C12N 9/16
[52] U.S. Cl. ...................... 435/196; 435/325; 435/320.1; 435/252.3; 435/348; 435/365; 435/358; 435/419; 514/44; 536/23.2; 536/23.1
[58] Field of Search ................................. 536/23.2, 23.1; 435/196, 325, 320.1, 252.3, 348, 365, 358, 419; 514/44

[56] References Cited

PUBLICATIONS

S. Adkins, et al., "Molecular Basis for the Polymorphic forms of Human Serum Paraoxonase/Arylesterase: Glutamine or Arginie at Position 191, for the Respective A or B allozymes," *American Journal of Human Genetics*, 52:598–608 (1993).

C.E. Furlong, et al., "Human and Rabbit Paraoxonases: Purification, Cloning, Sequencing, Mapping and Role of Polymorphism in Organophosphorus Detoxification," *Chem.–Biol. Interactions*. 87:35–48 (1993).

Hasset et al. (1991) Biochemistry 30(42):10141–10149.

La Du et al. (1987) Chem. Biol. Interactions 87:25–34.

Shaw et al. (1994) Biochem. J. 298(3):675–680.

Adkins et al. (1993) FASEB J. 7(4):A803.

Smolen A. et al., Drug Metabolism and Disposition, vol. 19:107–112 (1991).

Humbert, R. et al., Nature Genetics, vol. 3:73–76 (1993).

*Primary Examiner*—Rebecca E. Prouty
*Attorney, Agent, or Firm*—Human Genome Sciences, Inc.

[57] ABSTRACT

Human paraoxonase enzyme and DNA (RNA) encoding such paraoxonase enzymes are disclosed. Also provided is the procedure for producing such polypeptides by recombinant techniques. Uses of such polypeptides include their use as an antidote for organophosphate poisoning and to prevent neuronal cell death.

52 Claims, 2 Drawing Sheets

FIGURE 1A

```
  1 GGCACGAGAGCGAGGCAGCGCGCCCGGCTCCCGCGCCATGGGGCGGCTGGTGGCTGTGGG  60
  1                                       M   G   R   L   V   A   V   G  8

61 CTTGCTGGGGATCGCGCTGGCGCTCCTGGGCGAGAGGCTTCTGGCACTCAGAAATCGACT 120
  9  L   L   G   I   A   L   A   L   L   G   E   R   L   L   A   L   R   N   R   L  28

121 TAAAGCCTCCAGAGAAGTAGAATCTGTAGACCTTCCACACTGCCACCTGATTAAAGGAAT 180
 29  K   A   S   R   E   V   E   S   V   D   L   P   H   C   H   L   I   K   G   I  48

181 TGAAGCTGGCTCTGAAGATATTGACATACTTCCCAATGGTCTGGCTTTTTTTAGTGTGGG 240
 49  E   A   G   S   E   D   I   D   I   L   P   N   G   L   A   F   F   S   V   G  68

241 TCTAAAATTCCCAGGACTCCACAGCTTTGCACCAGATAAGCCTGGAGGAATACTAATGAT 300
 69  L   K   F   P   G   L   H   S   F   A   P   D   K   P   G   G   I   L   M   M  88

301 GGATCTAAAAGAAGAAAAACCAAGGGCACGGGAATTAAGAATCAGTCGTGGGTTTGATTT 360
 89  D   L   K   E   E   K   P   R   A   R   E   L   R   I   S   R   G   F   D   L 108

361 GGCCTCATTCAATCCACATGGCATCAGCACTTTCATAGACAACGATGACACAGTTTATCT 420
109  A   S   F   N   P   H   G   I   S   T   F   I   D   N   D   D   T   V   Y   L 128

421 CTTTGTTGTAAACCACCCAGAATTCAAGAATACAGTGGAAATTTTTAAATTTGAAGAAGC 480
129  F   V   V   N   H   P   E   F   K   N   T   V   E   I   F   K   F   E   E   A 148

481 AGAAAATTCTCTGTTGCATCTGAAAACAGTCAAACATGAGCTTCTTCCAAGTGTGAATGA 540
149  E   N   S   L   L   H   L   K   T   V   K   H   E   L   L   P   S   V   N   D 168

541 CATCACAGCTGTTGGACCGGCACATTTCTATGCCACAAATGACCACTACTTCTCTGATCC 600
169  I   T   A   V   G   P   A   H   F   Y   A   T   N   D   H   Y   F   S   D   P 188

601 TTTCTTAAAGTATTTAGAAACATACTTGAACTTACACTGGGCAAATGTTGTTTACTACAG 660
189  F   L   K   Y   L   E   T   Y   L   N   L   H   W   A   N   V   V   Y   Y   S 208

661 TCCAAATGAAGTTAAAGTGGTAGCAGAAGGATTTGATTCAGCAAATGGGATCAATATTTC 720
209  P   N   E   V   K   V   V   A   E   G   F   D   S   A   N   G   I   N   I   S 228
```

FIGURE 1B

```
721  ACCTGATGATAAGTATATCTATGTTGCTGACATATTGGCTCATGAAATTCATGTTTTGGA 780
229    P  D  D  K  Y  I  Y  V  A  D  I  L  A  H  E  I  H  V  L  E  248

781  AAAACACACTAATATGAATTTAACTCAGTTGAAGGTACTTGAGCTGGATACACTGGTGGA 840
249    K  H  T  N  M  N  L  T  Q  L  K  V  L  E  L  D  T  L  V  D  268

841  TAATTTATCTATTGATCCTTCCTCGGGGGACATCTGGGTAGGCTGTCATCCTAATGGCCA 900
269    N  L  S  I  D  P  S  S  G  D  I  W  V  G  C  H  P  N  G  Q  288

901  GAAGCTCTTCGTGTATGACCCGAACAATCCTCCCTCGTCAGAGGTTCTCCGCATCCAGAA 960
289    K  L  F  V  Y  D  P  N  N  P  P  S  S  E  V  L  R  I  Q  N  308

961  CATTCTATCTGAGAAGCCTACAGTGACTACAGTTTATGCCAACAATGGGTCTGTTCTCCA 1020
309    I  L  S  E  K  P  T  V  T  T  V  Y  A  N  N  G  S  V  L  Q  328

1021 AGGAAGTTCTGTAGCCTCAGTGTATGATGGGAAGCTGCTCATAGGCACTTTATACCACAG 1080
329    G  S  S  V  A  S  V  Y  D  G  K  L  L  I  G  T  L  Y  H  R  348

1081 AGCCTTGTATTGTGAACTCTAA 1102
349    A  L  Y  C  E  L  *   354
```

POLYNUCLEOTIDES ENCODING PARAOXONASE

This application is a divisional of application Ser. No. 08/783,889, filed Jan. 16, 1997, now U.S. Pat. No. 5,792,639, which is a divisional of application Ser. No. 08/270,583, filed Jul. 5, 1994, now U.S. Pat. No. 5,629,193.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is paraoxonase. The invention also relates to inhibiting the action of such polypeptides.

Parathion (diethyl-para-nitrophenyl phosphothioate) and chlorpyrifos (O, O-diethyl-O-3, 5, 6-trichloro-2-pyridinol), are commonly used organophosphorous insecticides and are involved in a large number of poisonings of agricultural workers and others each year (Hayes, W. J., Pesticides Studied in Man, Wilkins and Wilkins, Baltimore, pp. 284–435 (1982)). Both compounds are bioactivated in vivo to form the respective toxic oxon inhibitors of cholinesterase. This leads to neuronal cell death and related neuronal disorders. Both oxons are hydrolyzed by the enzyme paraoxonase/arylesterase, most, if not all, of which is located in the high-density lipoprotein (HDL) particles (Mackness, M. I., et al., Biochem. Pharmacol., 32:2291–2296 (1983)).

In humans, this enzyme exhibits a substrate dependent activity polymorphism (Mallinckrodt, M. G. and Diepgen, T. L., Toxicol. Environ. Chem., 18:79–196 (1988)). Human paraoxonase/arylesterase catalyzes the hydrolysis of organophosphates, aromatic carboxylic acid esters, and carbamates. There appears to be an existence of two alleles. One allelic product hydrolyses paraoxon with a high turnover number and the other with a low turnover number. Other substrates such as phenylacetate, beta and naphthylacetate (Gan, K. N., et al., Drug Metab. Dispos., 19:100–106 (1991)) and chlorpyrifos oxon (Furlong, C. E., et al., Anal. Biochem., 180:242–247 (1989)) are hydrolyzed by either allelic product at the same or nearly the same rate. The enzyme also hydrolyses the nerve agents soman and sarin (Gan, K. N., et al., Drug Metab. Dispos., 19:100–106 (1991)). The hydrolysis of neurotoxic organophosphates is a beneficial, fortuitous activity of paraoxonase.

In accordance with one aspect of the present invention, there is provided a novel putative mature polypeptide which is paraoxonase, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptide, or polynucleotide encoding such polypeptide for therapeutic purposes, for example, as an antidote for organophosphate toxicity (pesticide poisoning) and in preventing neuronal cell death.

In accordance with yet a further aspect of the present invention, there are provided antibodies against such polypeptides.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1A (sheet 1/2) and FIG. 1B (sheet 2/2), with FIG. 1B continuing the sequence information of FIG. 1A, collectively show the cDNA sequence (SEQ ID NO:1) and deduced amino acid sequence (SEQ ID NO:2) for the putative mature paraoxonase polypeptide. The standard one-letter abbreviations for amino acids are utilized.

In accordance with an aspect of the present invention, there is provided an isolated nucleic acid (polynucleotide) which encodes for the mature polypeptide having the deduced amino acid sequence of FIGS. 1A–1B or for the mature polypeptide encoded by the cDNA of the clone deposited as ATCC Deposit No. 75773 on May 12, 1994.

The polynucleotide of this invention was discovered in a cDNA library derived from a human amygdala. It is structurally related to the human paraoxonase/arylesterase family. It contains an open reading frame encoding a protein of approximately 356 amino acid residues. The protein exhibits the highest degree of homology to paraoxonase of oryctolagus cuniculus with 67% identity and 83% similarity over a 249 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1B or that of the deposited clone or may be a different coding sequence which coding sequence, as a result of the redundancy or degeneracy of the genetic code, encodes the same mature polypeptide as the DNA of FIGS. 1A–1B or the deposited cDNA.

The polynucleotide which encodes for the mature polypeptide of FIGS. 1A–1B or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1B or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1B or the same mature polypeptide encoded by the cDNA of the deposited clone as well as variants of such polynucleotides which variants encode for a fragment, derivative or analog of the polypeptide of FIGS. 1A–1B or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1B or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIGS. 1A–1B or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted. However, if a patent should issue directed to the present invention, upon the issuance of such a patent the deposited strain of ATCC 75773 will irrevocably and without restriction be released to the public.

The present invention further relates to a paraoxonase polypeptide which has the deduced amino acid sequence of FIGS. 1A–1B or which has the amino acid sequence encoded by the deposited cDNA, as well as fragments, analogs and derivatives of such polypeptide.

The terms "fragment," "derivative" and "analog" when referring to the polypeptide of FIGS. 1A–1B or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1B or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the paraoxonase genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, $Salmonella$ $typhimurium$; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The paraoxonase polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The paraoxonase polypeptides of the present invention are useful as an antidote for organophosphate poisoning, since the toxic oxon inhibitors of cholinesterase are hydrolyzed by paraoxonase.

The paraoxonase polypeptides are also useful for preventing neuronal cell death due to such toxic poisoning. If organophosphate poisoning is left untreated, neuronal cell death will result.

The polypeptide of the present invention is also useful for identifying other molecules which have similar biological activity. An example of a screen for this is isolating the coding region of the paraoxonase gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. Paraoxonase is administered in an amount which is effective for treating and/or prophylaxis of the specific indication. In general, Paraoxonase will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. The paraoxonase gene is located close to the cystic fibrosis gene on chromosome 7. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

This invention also provides a method of screening drugs to identify those which enhance (agonists) the interaction of paraoxonase with its substrate which comprises, for example, contacting a mammalian cell comprising a DNA molecule encoding paraoxonase with a plurality of drugs and parathion or chlorpyrifos and detecting those drugs which enhance the hydrolysis of the toxic oxons by paraoxonase and thereby identifying drugs which specifically act as agonists. Various methods of detection may be employed. The toxic oxons may be "labeled" by association with a detectable marker substance (e.g., radiolabel or a non-isotopic label, such as biotin) such that their hydrolysis may be measured. Drug candidates are identified by choosing chemical compounds which bind with high affinity to the expressed paraoxonase polypeptide in transfected cells, using radioligand binding methods well-known in the art.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide or agarose gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Paraoxonase

The DNA sequence encoding for paraoxonase, ATCC #75773, is initially amplified using PCR oligonucleotide primers corresponding to the 5' and sequences of the processed paraoxonase protein (minus the signal peptide sequence) and the vector sequences 3' to the paraoxonase gene. Additional nucleotides corresponding to paraoxonase were added to the 5' and 3' sequences respectively. The 5' oligonucleotide primer has the sequence 5' TCAGGATC-CAGAAATCGACTTAAAGCCTCC 3' (SEQ ID NO:3) contains a Bam HI restriction enzyme site followed by 21 nucleotides of paraoxonase coding sequence starting from the presumed terminal amino acid of the processed protein codon. The 3' sequence 5' TCAAAGCTTTTAGAGTTCA-CAATACAAGGC 3' (SEQ ID NO:4) contains complementary sequences to a Hind III restriction site and is followed by 21 nucleotides of paraoxonase. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with Bam HI and Hind III. The amplified sequences were ligated into pQE-9 and were inserted in frame with the sequence encoding for the histidine tag and the RBS. FIGS. 1A–1B show a schematic representation of this arrangement. The ligation mixture was then used to transform E. coli strain SURE (available from Stratagene Cloning Systems, 11099 North Torrey Pines Road, La Jolla, Calif. 92037) by the procedure described in Sambrook, J. et al., Molecular Cloning: A Laboratory Manual, Cold Spring Laboratory Press, (1989). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized paraoxonase was purified from this solution by chromatography on a Nickel-Chelate column under conditions that allow for tight binding by proteins containing the 6-His tag. Hochuli, E. et al., J. Chromatography 411:177–184 (1984). Paraoxonase was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant Paraoxonase in CHO Cells

The expression of plasmid, paraoxonase HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire paraoxonase precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding for paraoxonase, ATCC #75773, was constructed by PCR on the original EST cloned using two primers: the 5' primer 5' CGCGGGATCCAC-CATGGGGGCGGCTGGTGGCTCT 3' (SEQ ID NO:5) contains a Bam HI restriction site followed by 21 nucleotides of paraoxonase coding sequence starting from the initiation codon; the 3' sequence 5' CGCGTCTAGACGGT- TAGAGTTCACAATACAAGGC 3' (SEQ ID NO:6) contains complementary sequences to an Xba I site and a translation stop codon and the last 18 nucleotides of the paraoxonase coding sequence (not including the stop codon). Therefore, the PCR product contains a Bam HI site, paraoxonase coding sequence, a translation termination stop codon and an Xba I site. The PCR amplified DNA fragment and the vector, pcDNAI/Amp, were digested with Bam HI and Xba I restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant paraoxonase, CHO cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the paraoxonase HA protein was detected by radio-labelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Expression Pattern of Paraoxonase in Human Tissue

Northern blot analysis is carried out to examine the levels of expression of paraoxonase in human tissues. Total cellular RNA samples are isolated with RNAzol™ B system (Biotecx Laboratories, Inc. 6023 South Loop East, Houston, Tex. 77033). About 10 μg of total RNA isolated from each human tissue specified is separated on 1% agarose gel and blotted onto a nylon filter. (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column. (5 Prime—3 Prime, Inc. 5603 Arapahoe Road, Boulder, Colo. 80303). The filter is then hybridized with radioactive labeled full length paraoxonase gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter is then exposed at −70° C. overnight with an intensifying screen.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence encoding amino acids +25 to +356 of SEQ ID NO:2.

2. The isolated polynucleotide of claim 1, wherein said nucleic acid sequence comprises nucleotides 76 to 1071 of SEQ ID NO:1.

3. An isolated polynucleotide complementary to the polynucleotide of claim 1.

4. The isolated polynucleotide of claim 1 further comprising a heterologous polynucleotide.

5. The isolated polynucleotide of claim 4, wherein the heterologous polynucleotide encodes a heterologous polypeptide.

6. A vector comprising the polynucleotide of claim 1.

7. A host cell comprising the polynucleotide of claim 1 operably associated with a heterologous regulatory sequence.

8. A method of producing a polypeptide comprising:

(a) culturing the host cell of claim 7 under conditions such that the polypeptide is expressed; and (b) recovering said polypeptide.

9. A composition comprising the isolated polynucleotide of claim 1.

10. The isolated polynucleotide of claim 1, wherein said nucleic acid sequence encodes amino acids +2 to +356 of SEQ ID NO:2.

11. The isolated polynucleotide of claim 10, wherein said nucleic acid sequence comprises nucleotides 7 to 1071 of SEQ ID NO:1.

12. An isolated polynucleotide complementary to the polynucleotide of claim 10.

13. The isolated polynucleotide of claim 10 further comprising a heterologous polynucleotide.

14. The isolated polynucleotide of claim 13, wherein the heterologous polynucleotide encodes a heterologous polypeptide.

15. A vector comprising the polynucleotide of claim 10.

16. A host cell comprising the polynucleotide of claim 10 operably associated with a heterologous regulatory sequence.

17. A method of producing a polypeptide comprising:

(a) culturing the host cell of claim 16 under conditions such that the polypeptide is expressed; and (b) recovering said polypeptide.

18. A composition comprising the isolated polynucleotide of claim 10.

19. The isolated polynucleotide of claim 1, wherein said nucleic acid sequence encodes amino acids +1 to +356 of SEQ ID NO:2.

20. The isolated polynucleotide of claim 19, wherein said nucleic acid sequence comprises nucleotides 4 to 1071 of SEQ ID NO:1.

21. An isolated polynucleotide complementary to the polynucleotide of claim 19.

22. The isolated polynucleotide of claim 19 further comprising a heterologous polynucleotide.

23. The isolated polynucleotide of claim 22, wherein the heterologous polynucleotide encodes a heterologous polypeptide.

24. A vector comprising the polynucleotide of claim 19.

25. A host cell comprising the polynucleotide of claim 19 operably associated with a heterologous regulatory sequence.

26. A method of producing a polypeptide comprising:

(a) culturing the host cell of claim 25 under conditions such that the polypeptide is expressed; and (b) recovering said polypeptide.

27. A composition comprising the isolated polynucleotide of claim 19.

28. A host cell comprising an isolated polynucleotide comprising a nucleic acid sequence encoding the mature portion of the protein encoded by the cDNA contained in ATCC Deposit No. 75773 operably associated with a heterologous regulatory sequence.

29. A method of producing a polypeptide comprising:

(a) culturing the host cell of claim 28 under conditions such that the polypeptide is expressed; and (b) recovering said polypeptide.

30. A composition comprising an isolated polynucleotide comprising a nucleic acid sequence encoding the mature portion of the protein encoded by the cDNA contained in ATCC Deposit No. 75773 and a pharmaceutically acceptable carrier.

31. An isolated polynucleotide comprising a nucleic acid sequence encoding the complete amino acid sequence encoded by the cDNA contained in ATCC Deposit No. 75773.

32. The isolated polynucleotide of claim 31 further comprising a heterologous polynucleotide.

33. The isolated polynucleotide of claim 32, wherein the heterologous polynucleotide encodes a heterologous polypeptide.

34. A vector comprising the polynucleotide of claim 31.

35. A host cell comprising the polynucleotide of claim 31 operably associated with a heterologous regulatory sequence.

36. A method of producing a polypeptide comprising:
   (a) culturing the host cell of claim 35 under conditions such that the polypeptide is expressed; and
   (b) recovering said polypeptide.

37. A composition comprising the isolated polynucleotide of claim 31.

38. An isolated polynucleotide comprising a nucleic acid sequence encoding a polypeptide fragment of SEQ ID NO:2 or a polypeptide fragment encoded by the cDNA contained in ATCC Deposit No. 75773, wherein said fragment has paraoxonase activity.

39. An isolated polynucleotide complementary to the polynucleotide of claim 38.

40. The isolated polynucleotide of claim 38 further comprising a heterologous polynucleotide.

41. The isolated polynucleotide of claim 40, wherein the heterologous polynucleotide encodes a heterologous polypeptide.

42. A vector comprising the polynucleotide of claim 38.

43. A host cell comprising the polynucleotide of claim 38 operably associated with a heterologous regulatory sequence.

44. A method of producing a polypeptide comprising:
   (a) culturing the host cell of claim 43 under conditions such that the polypeptide is expressed; and
   (b) recovering said polypeptide.

45. A composition comprising the isolated polynucleotide of claim 38.

46. An isolated polynucleotide comprising a nucleic acid sequence that hybridizes to a polynucleotide consisting of SEQ ID NO:1, the complement thereof, or the cDNA contained in ATCC Deposit No. 75773 under hybridization conditions comprising hybridization in a wash buffer consisting of 0.5×SSC and 0.1% SDS at 60° C.

47. An isolated polynucleotide complementary to the polynucleotide of claim 46.

48. The isolated polynucleotide of claim 46 further comprising a heterologous polynucleotide.

49. The isolated polynucleotide of claim 48, wherein the heterologous polynucleotide encodes a heterologous polypeptide.

50. A vector comprising the polynucleotide of claim 46.

51. A host cell comprising the polynucleotide of claim 46 operably associated with a heterologous regulatory sequence.

52. A composition comprising the isolated polynucleotide of claim 46.

* * * * *

SEQUENCE LISTING

<160> NUMBER OF SEQ ID NOS: 6

<210> SEQ ID NO 1
<211> LENGTH: 1102
<212> TYPE: DNA
<213> ORGANISM: Homo sapiens
<220> FEATURE:
<221> NAME/KEY: CDS
<222> LOCATION: (38)..(1102)

<400> SEQUENCE: 1

```
ggcacgagag cgaggcagcg cgcccggctc ccgcgcc atg ggg cgg ctg gtg gct      55
                                        Met Gly Arg Leu Val Ala
                                        1               5 gtg ggc ttg ctg ggg atc gcg ctg gcg ctc ctg ggc gag agg ctt ctg      103
Val Gly Leu Leu Gly Ile Ala Leu Ala Leu Leu Gly Glu Arg Leu Leu
            10                  15                  20 gca ctc aga aat cga ctt aaa gcc tcc aga gaa gta gaa tct gta gac      151
Ala Leu Arg Asn Arg Leu Lys Ala Ser Arg Glu Val Glu Ser Val Asp
        25                  30                  35 ctt cca cac tgc cac ctg att aaa gga att gaa gct ggc tct gaa gat      199
Leu Pro His Cys His Leu Ile Lys Gly Ile Glu Ala Gly Ser Glu Asp
    40                  45                  50 att gac ata ctt ccc aat ggt ctg gct ttt ttt agt gtg ggt cta aaa      247
Ile Asp Ile Leu Pro Asn Gly Leu Ala Phe Phe Ser Val Gly Leu Lys
55                  60                  65                  70 ttc cca gga ctc cac agc ttt gca cca gat aag cct gga gga ata cta      295
Phe Pro Gly Leu His Ser Phe Ala Pro Asp Lys Pro Gly Gly Ile Leu
                75                  80                  85 atg atg gat cta aaa gaa gaa aaa cca agg gca cgg gaa tta aga atc      343
```

```
Met Met Asp Leu Lys Glu Glu Lys Pro Arg Ala Arg Glu Leu Arg Ile
            90                  95                 100 agt cgt ggg ttt gat ttg gcc tca ttc aat cca cat ggc atc agc act    391
Ser Arg Gly Phe Asp Leu Ala Ser Phe Asn Pro His Gly Ile Ser Thr
            105                 110                115 ttc ata gac aac gat gac aca gtt tat ctc ttt gtt gta aac cac cca    439
Phe Ile Asp Asn Asp Asp Thr Val Tyr Leu Phe Val Val Asn His Pro
        120                 125                 130 gaa ttc aag aat aca gtg gaa att ttt aaa ttt gaa gaa gca gaa aat    487
Glu Phe Lys Asn Thr Val Glu Ile Phe Lys Phe Glu Glu Ala Glu Asn
135                 140                 145                 150 tct ctg ttg cat ctg aaa aca gtc aaa cat gag ctt ctt cca agt gtg    535
Ser Leu Leu His Leu Lys Thr Val Lys His Glu Leu Leu Pro Ser Val
                155                 160                 165 aat gac atc aca gct gtt gga ccg gca cat ttc tat gcc aca aat gac    583
Asn Asp Ile Thr Ala Val Gly Pro Ala His Phe Tyr Ala Thr Asn Asp
            170                 175                 180 cac tac ttc tct gat cct ttc tta aag tat tta gaa aca tac ttg aac    631
His Tyr Phe Ser Asp Pro Phe Leu Lys Tyr Leu Glu Thr Tyr Leu Asn
            185                 190                 195 tta cac tgg gca aat gtt gtt tac tac agt cca aat gaa gtt aaa gtg    679
Leu His Trp Ala Asn Val Val Tyr Tyr Ser Pro Asn Glu Val Lys Val
        200                 205                 210 gta gca gaa gga ttt gat tca gca aat ggg atc aat att tca cct gat    727
Val Ala Glu Gly Phe Asp Ser Ala Asn Gly Ile Asn Ile Ser Pro Asp
215                 220                 225                 230 gat aag tat atc tat gtt gct gac ata ttg gct cat gaa att cat gtt    775
Asp Lys Tyr Ile Tyr Val Ala Asp Ile Leu Ala His Glu Ile His Val
                235                 240                 245 ttg gaa aaa cac act aat atg aat tta act cag ttg aag gta ctt gag    823
Leu Glu Lys His Thr Asn Met Asn Leu Thr Gln Leu Lys Val Leu Glu
            250                 255                 260 ctg gat aca ctg gtg gat aat tta tct att gat cct tcc tcg ggg gac    871
Leu Asp Thr Leu Val Asp Asn Leu Ser Ile Asp Pro Ser Ser Gly Asp
            265                 270                 275 atc tgg gta ggc tgt cat cct aat ggc cag aag ctc ttc gtg tat gac    919
Ile Trp Val Gly Cys His Pro Asn Gly Gln Lys Leu Phe Val Tyr Asp
        280                 285                 290 ccg aac aat cct ccc tcg tca gag gtt ctc cgc atc cag aac att cta    967
Pro Asn Asn Pro Pro Ser Ser Glu Val Leu Arg Ile Gln Asn Ile Leu
295                 300                 305                 310 tct gag aag cct aca gtg act aca gtt tat gcc aac aat ggg tct gtt   1015
Ser Glu Lys Pro Thr Val Thr Thr Val Tyr Ala Asn Asn Gly Ser Val
                315                 320                 325 ctc caa gga agt tct gta gcc tca gtg tat gat ggg aag ctg ctc ata   1063
Leu Gln Gly Ser Ser Val Ala Ser Val Tyr Asp Gly Lys Leu Leu Ile
            330                 335                 340 ggc act tta tac cac aga gcc ttg tat tgt gaa ctc taa               1102
Gly Thr Leu Tyr His Arg Ala Leu Tyr Cys Glu Leu
            345                 350                 355

<210> SEQ ID NO 2
<211> LENGTH: 354
<212> TYPE: PRT
<213> ORGANISM: Homo sapiens

<400> SEQUENCE: 2

Met Gly Arg Leu Val Ala Val Gly Leu Leu Gly Ile Ala Leu Ala Leu
  1               5                  10                  15

Leu Gly Glu Arg Leu Leu Ala Leu Arg Asn Arg Leu Lys Ala Ser Arg
```

```
            20                  25                  30
Glu Val Glu Ser Val Asp Leu Pro His Cys His Leu Ile Lys Gly Ile
         35                  40                  45
Glu Ala Gly Ser Glu Asp Ile Asp Ile Leu Pro Asn Gly Leu Ala Phe
     50                  55                  60
Phe Ser Val Gly Leu Lys Phe Pro Gly Leu His Ser Phe Ala Pro Asp
 65                  70                  75                  80
Lys Pro Gly Gly Ile Leu Met Met Asp Leu Lys Glu Lys Pro Arg
                 85                  90                  95
Ala Arg Glu Leu Arg Ile Ser Arg Gly Phe Asp Leu Ala Ser Phe Asn
                100                 105                 110
Pro His Gly Ile Ser Thr Phe Ile Asp Asn Asp Thr Val Tyr Leu
                115                 120                 125
Phe Val Val Asn His Pro Glu Phe Lys Asn Thr Val Glu Ile Phe Lys
    130                 135                 140
Phe Glu Glu Ala Glu Asn Ser Leu Leu His Leu Lys Thr Val Lys His
145                 150                 155                 160
Glu Leu Leu Pro Ser Val Asn Asp Ile Thr Ala Val Gly Pro Ala His
                165                 170                 175
Phe Tyr Ala Thr Asn Asp His Tyr Phe Ser Asp Pro Phe Leu Lys Tyr
                180                 185                 190
Leu Glu Thr Tyr Leu Asn Leu His Trp Ala Asn Val Val Tyr Tyr Ser
                195                 200                 205
Pro Asn Glu Val Lys Val Val Ala Glu Gly Phe Asp Ser Ala Asn Gly
                210                 215                 220
Ile Asn Ile Ser Pro Asp Asp Lys Tyr Ile Tyr Val Ala Asp Ile Leu
225                 230                 235                 240
Ala His Glu Ile His Val Leu Glu Lys His Thr Asn Met Asn Leu Thr
                245                 250                 255
Gln Leu Lys Val Leu Glu Leu Asp Thr Leu Val Asp Asn Leu Ser Ile
                260                 265                 270
Asp Pro Ser Ser Gly Asp Ile Trp Val Gly Cys His Pro Asn Gly Gln
                275                 280                 285
Lys Leu Phe Val Tyr Asp Pro Asn Asn Pro Pro Ser Ser Glu Val Leu
                290                 295                 300
Arg Ile Gln Asn Ile Leu Ser Glu Lys Pro Thr Val Thr Thr Val Tyr
305                 310                 315                 320
Ala Asn Asn Gly Ser Val Leu Gln Gly Ser Ser Val Ala Ser Val Tyr
                325                 330                 335
Asp Gly Lys Leu Leu Ile Gly Thr Leu Tyr His Arg Ala Leu Tyr Cys
                340                 345                 350
Glu Leu

<210> SEQ ID NO 3
<211> LENGTH: 30
<212> TYPE: DNA
<213> ORGANISM: Homo sapiens

<400> SEQUENCE: 3
tcaggatcca gaaatcgact taaagcctcc                                    30

<210> SEQ ID NO 4
<211> LENGTH: 30
<212> TYPE: DNA
<213> ORGANISM: Homo sapiens
```

```
<400> SEQUENCE: 4
tcaaagcttt tagagttcac aatacaaggc                                                30

<210> SEQ ID NO 5
<211> LENGTH: 34
<212> TYPE: DNA
<213> ORGANISM: Homo sapiens

<400> SEQUENCE: 5
cgcgggatcc accatggggg cggctggtgg ctct                                           34

<210> SEQ ID NO 6
<211> LENGTH: 34
<212> TYPE: DNA
<213> ORGANISM: Homo sapiens

<400> SEQUENCE: 6
cgcgtctaga cggttagagt tcacaataca aggc                                           34
```